(12) United States Patent
Minas et al.

(10) Patent No.: US 11,980,723 B2
(45) Date of Patent: May 14, 2024

(54) SUPPORT MEMBER FOR INTRALUMINAL IMAGING DEVICES AND ASSOCIATED DEVICES, SYSTEMS, AND METHODS

(71) Applicant: KONINKLIJKE PHILIPS N.V., Eindhoven (NL)

(72) Inventors: Maritess Minas, San Diego, CA (US); Jeremy Stigall, Carlsbad, CA (US); Princeton Saroha, Ladera Ranch, CA (US); Melisa Friday, San Diego, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 173 days.

(21) Appl. No.: 16/611,309

(22) PCT Filed: May 3, 2018

(86) PCT No.: PCT/EP2018/061239
§ 371 (c)(1),
(2) Date: Nov. 6, 2019

(87) PCT Pub. No.: WO2018/206369
PCT Pub. Date: Nov. 15, 2018

(65) Prior Publication Data
US 2020/0163651 A1 May 28, 2020

Related U.S. Application Data

(60) Provisional application No. 62/504,600, filed on May 11, 2017.

(51) Int. Cl.
*A61B 8/08* (2006.01)
*A61B 8/00* (2006.01)
(Continued)

(52) U.S. Cl.
CPC ......... *A61M 25/0069* (2013.01); *A61B 8/445* (2013.01); *A61B 8/12* (2013.01);
(Continued)

(58) Field of Classification Search
None
See application file for complete search history.

(56) References Cited

U.S. PATENT DOCUMENTS 5,354,220 A    10/1994  Ganguly
5,596,991 A *   1/1997  Tanaka ..................... A61B 8/12
                                                  600/459
(Continued)

FOREIGN PATENT DOCUMENTS

EP      0671221         9/1995
JP      2004305333 A    11/2004
WO      99/16347        4/1999

OTHER PUBLICATIONS

International Search Report and Written Opinion dated Aug. 14, 2018 for International Application No. PCT/EP2018/061239 Filed May 3, 2018.

*Primary Examiner* — Christopher Koharski
*Assistant Examiner* — Renee C Langhals

(57) ABSTRACT

An intraluminal imaging device is provided that includes a flexible elongate member (115) configured for positioning within a body lumen of a patient, a support member (300) coupled to the flexible elongate member, and an imaging assembly (110) coupled to the support member. The support member can include a proximal section (310) configured to interface with a distal portion of the flexible elongate member and a distal section (320) configured to interface with a proximal end of the imaging assembly, wherein the proximal section has a first diameter and the distal section has a second diameter less than the first diameter.

17 Claims, 10 Drawing Sheets

(51) Int. Cl.
  *A61B 8/12*   (2006.01)
  *A61M 25/00*  (2006.01)
  *B06B 1/02*   (2006.01)
  *H10N 30/87*  (2023.01)

(52) U.S. Cl.
  CPC . *A61M 2025/0004* (2013.01); *A61M 25/0009* (2013.01); *A61M 25/0052* (2013.01); *B06B 1/0207* (2013.01); *B06B 2201/20* (2013.01); *B06B 2201/76* (2013.01); *H10N 30/875* (2023.02)

(56) References Cited

U.S. PATENT DOCUMENTS

| | | | | |
|---|---|---|---|---|
| 6,017,311 A * | 1/2000 | Sakamoto | A61B 8/12 | 600/459 |
| 6,238,347 B1 * | 5/2001 | Nix | A61B 8/12 | 600/463 |
| 6,261,246 B1 * | 7/2001 | Pantages | A61B 8/12 | 600/459 |
| 6,641,540 B2 | 11/2003 | Fleischman | | |
| 6,776,763 B2 | 8/2004 | Nix | | |
| 7,226,417 B1 | 6/2007 | Eberle | | |
| 7,846,101 B2 | 12/2010 | Eberle | | |
| 2015/0305710 A1 * | 10/2015 | Stigall | A61B 8/0891 | 600/424 |
| 2016/0058382 A1 * | 3/2016 | Burkett | A61B 5/0215 | 600/486 |

\* cited by examiner

SUPPORT MEMBER FOR INTRALUMINAL IMAGING DEVICES AND ASSOCIATED DEVICES, SYSTEMS, AND METHODS

CROSS REFERENCE TO RELATED APPLICATIONS

This application is the U.S. National Phase application under 35 U.S.C. § 371 of International Application No. PCT/EP2018/061239 filed May 3, 2018, published as WO 2018/206369 on Nov. 15, 2018, which claims the benefit of U.S. Provisional Patent Application No. 62/504,600 filed May 11, 2017. These applications are hereby incorporated by reference herein.

TECHNICAL FIELD

The present disclosure relates generally to intraluminal imaging and, in particular, to connecting components of an intraluminal imaging device.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

Solid-state (also known as synthetic-aperture) IVUS catheters are one of the two types of IVUS devices commonly used today, the other type being the rotational IVUS catheter. Solid-state IVUS catheters carry a scanner assembly that includes an array of ultrasound transducers distributed around its circumference along with one or more integrated circuit controller chips mounted adjacent to the transducer array. The controllers select individual transducer elements (or groups of elements) for transmitting an ultrasound pulse and for receiving the ultrasound echo signal. By stepping through a sequence of transmit-receive pairs, the solid-state IVUS system can synthesize the effect of a mechanically scanned ultrasound transducer but without moving parts (hence the solid-state designation). Since there is no rotating mechanical element, the transducer array can be placed in direct contact with the blood and vessel tissue with minimal risk of vessel trauma. Furthermore, because there is no rotating element, the electrical interface is simplified. The solid-state scanner can be wired directly to the imaging system with a simple electrical cable and a standard detachable electrical connector, rather than the complex rotating electrical interface required for a rotational IVUS device.

The electrical cable and the solid-state scanner are connected during assembly of the IVUS device. Generally, this requires that conductors in the electrical cable be aligned with a respective conductive pad on the solid-state scanner and soldered together. Often the soldered connection of the conductors and the conductive pads is in proximity of a support member. The support member serves as the interface between a shaft of the catheter and the scanner assembly (or imaging assembly).

Traditionally the support member is cylindrical in shape with a uniform diameter that is approximately equal to the inner diameter of the shaft of the catheter. Further, an adhesive is applied to the junction between the support member and the imaging assembly to insulate the electrical connection from fluids, such as flood and saline and to provide additional mechanical strength. In this regard, because the adhesive is applied mostly to the outer surface of the shaft and the imaging assembly, the resulting seal is prone to fluid ingress and moisture exposure, causing breakdown of the imaging assembly. In addition, the resulting glob of the adhesive is shaped or smoothed by assembly operators by hand in an effort to define a relatively smooth transition across the joint between the shaft and the imaging assembly. This shaping and smoothing process is thus subject to high variation in the resulting outer profile of the device and integrity of the fluid seal from one assembly operator person to the next and even between devices assembled by the same operator. Furthermore, because the support member is usually made of stiff materials to provide structural strength at the junction, the junction of the shaft and the imaging assembly has limited flexibility, impacting the navigational capability of intraluminal imaging devices.

SUMMARY

Embodiments of the present disclosure provide a support member for interconnecting an imaging assembly and an outer catheter shaft in an intraluminal imaging device. At least a portion of the support member is placed within a distal portion of an outer catheter shaft and a distal end of the support member is in contact with a proximal end of the imaging assembly. The support member has a varying outer diameter along its length. A proximal section of the support member has a diameter larger than that of a distal section of the support member. That way, when the support member is at least partially positioned within the outer catheter shaft, the outer surface of the support member and the inner surface of the distal portion of the outer catheter shaft form an annular lumen. A gap is left between the distal end of the outer catheter shaft and the proximal end of the imaging assembly. The gap is in fluid communication with the annular lumen. Both the gap and the annular lumen are filled with an adhesive. The proximal section with a larger diameter contains the adhesive and prevents it from overflowing while the distal section with a smaller diameter allows for better adhesion by providing larger adhesion surface area for the adhesive. The annular lumen also improves assembly consistency and reproducibility of the assembly process by removing the process variability introduced by shaping and smoothing the adhesive by hand. After filling the gap and the annular lumen with the adhesive, no or minimum shaping and smoothing is required.

In one embodiment, an intraluminal imaging device is provided. The intraluminal imaging device comprises a flexible elongate member configured for positioning within a body lumen of a patient; a support member coupled to the flexible elongate member; and an imaging assembly coupled to the support member. The support member can include a proximal section configured to interface with a distal portion of the flexible elongate member and a distal section configured to interface with a proximal end of the imaging assembly, wherein the proximal section has a first diameter and the distal section has a second diameter less than the first diameter.

In some embodiments, the proximal section of the support member, the distal section of the support member, and the distal portion of the flexible elongate member define an annular lumen. In some embodiments, a distal end of the flexible elongate member is spaced from the proximal end of the imaging assembly by a gap and the gap is in fluid communication with the annular lumen. In some embodiments, the intraluminal imaging device further comprises an adhesive disposed within the annular lumen and the gap. In some embodiments, the support member comprises a lumen extending longitudinally through the proximal section and the distal section. In some embodiments, the imaging assembly comprises a tubular member and a flexible substrate positioned around the tubular member, and the lumen of the support member is configured to receive the tubular member. In some embodiments, the lumen of the support member is further configured to receive an inner member configured to receive a guidewire. In some embodiments, the support member further includes an opening extending through a wall in communication with the lumen, the opening configured to receive an electrical cable associated with the imaging assembly. In some embodiments, a connection interface of the imaging assembly is mounted to an outer surface of the support member. In some embodiments, the support member comprises a transition between the first diameter and the second diameter, the transition comprising a tapered region. In some embodiments, the imaging assembly comprises an ultrasound transducer array.

In some embodiments, a method of forming an intraluminal imaging device is provided. The method includes providing a support member comprising a proximal section with a first diameter and a distal section with a second diameter less than the first diameter; coupling a proximal portion of an imaging assembly to the distal section of the support member; positioning a flexible elongate member over the support member such that the proximal section of the support member, the distal section of the support member, and a distal portion of the flexible elongate member define an annular lumen; and filling the annular lumen with an adhesive.

In some embodiments, positioning a flexible elongate member over the support member includes spacing a distal end of the flexible elongate member from a proximal end of the imaging assembly by a gap, the gap being in fluid communication with the annular lumen. In some embodiments, a distal end of the support member is in direct contact with the proximal end of the imaging assembly when the distal end of the flexible elongate member is spaced from the proximal end of the imaging assembly by the gap. In some embodiments, filling the annular lumen with the adhesive includes supplying the adhesive through the gap and filling the gap. In some embodiments, filling the annular lumen with the adhesive comprises forming an outer surface of the adhesive, and the outer surface of the adhesive is coplanar with an outer surface of the proximal section of the imaging assembly and an outer surface of the distal portion of the flexible elongate member. In some embodiments, the support member comprises a lumen extending longitudinally through the proximal and distal sections, the imaging assembly comprises a tubular member, and coupling the proximal portion of the imaging assembly to the distal section of the support member includes inserting the tubular member into the lumen. In some embodiments, the method further comprises coupling a connection interface of the imaging assembly with an electrical cable. In some embodiments, coupling the connection interface of the imaging assembly with the electrical cable includes: threading the electrical cable into a lumen extending longitudinally through the distal and proximal sections of the support member through an opening positioned in the proximal section of the support member; and electrically bonding the electrical cable to the connection interface near the proximal section of the support member.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
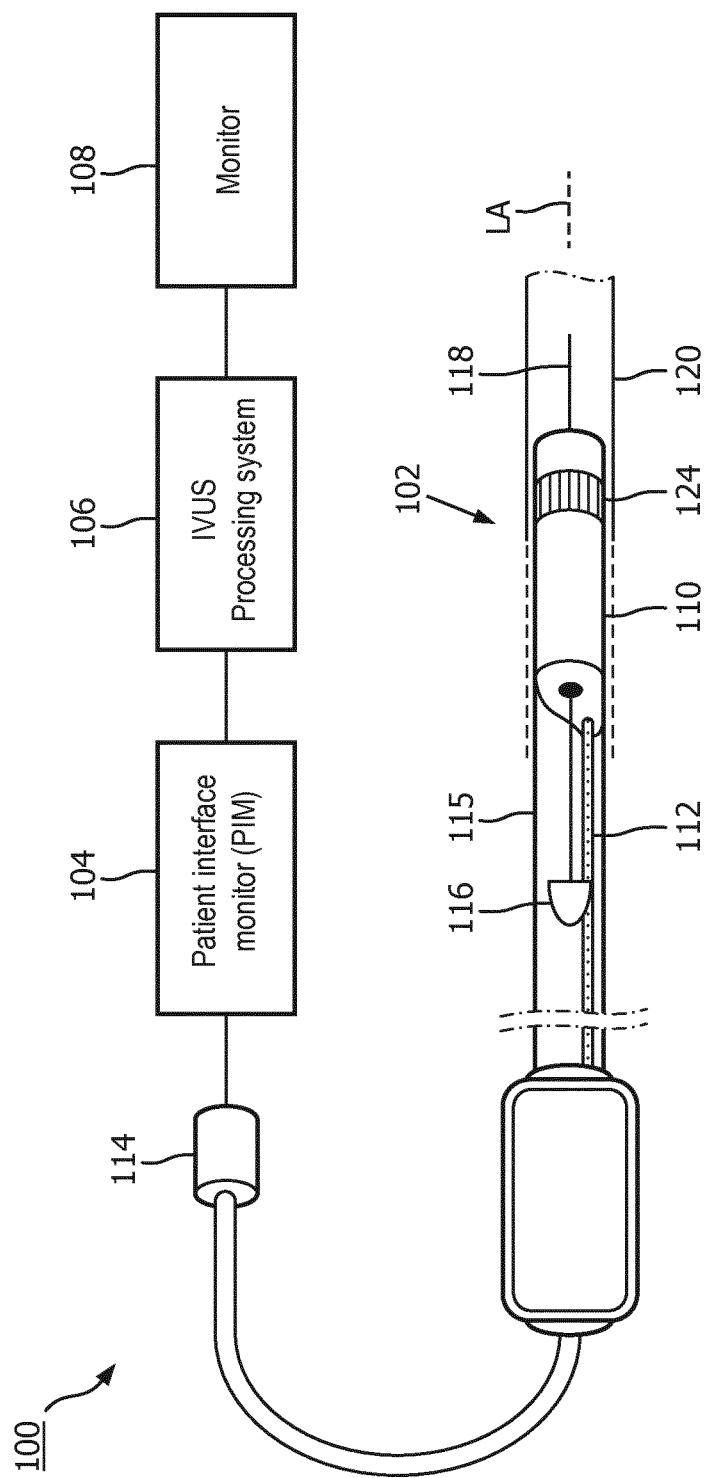
FIG. 1 is a diagrammatic schematic view of an imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

The intraluminal imaging devices described herein achieve numerous advantages. For example, a support member of the intraluminal imaging devices according to aspects of the present disclosure facilitate a faster, less labor-intensive, more consistent, and more efficient manufacturing process for the intraluminal device. Additionally, coupling a flexible elongate member to an imaging assembly using the support member creates a more robust imaging assembly less prone to breakage and fluid ingress. For example, because a diameter of a distal section of the support member is smaller than a proximal section of the support member, an annular lumen is formed between an outer surface of the support member and an inner surface of a distal portion of the flexible elongate member. The annular lumen provides more adhesion surface for adhesive, resulting in a more robust coupling between support member, the flexible elongate member, and the imaging assembly. That way, the adhesive can form a stronger bather of fluid. An intraluminal imaging device according to the present disclosure has improved navigational capability for at least the following reasons. The adhesive in the annular lumen introduce flexibility and tensile strength to the junction between the flexible elongate member and the imaging assembly. In addition, as the annular lumen provides adhesion surface for the adhesive, no or minimum adhesive needs to be on the outer surface of the junction between the flexible elongate member and the imaging assembly. As a result, the resulting junction has a lower profile that contributes to navigational capability.

FIG. 1 is a diagrammatic schematic view of an intravascular ultrasound (IVUS) imaging system 100, according to aspects of the present disclosure. The IVUS imaging system 100 may include a solid-state IVUS device 102 such as a catheter, guide wire, or guide catheter, a patient interface module (PIM) 104, an IVUS processing system or console 106, and a monitor 108.

At a high level, the IVUS device 102 emits ultrasonic energy from a transducer array 124 included in imaging assembly 110 mounted near a distal end of the catheter device. The ultrasonic energy is reflected by tissue structures in the medium, such as a vessel 120, surrounding the imaging assembly 110, and the ultrasound echo signals are received by the transducer array 124. The PIM 104 transfers the received echo signals to the processing system 106 where the ultrasound image (including the flow information) is reconstructed and displayed on the monitor 108. The processing system 106 can include a processor and a memory. The processing system 106 can be operable to facilitate the features of the IVUS imaging system 100 described herein. For example, the processor can execute computer readable instructions stored on the non-transitory tangible computer readable medium.

The PIM 104 facilitates communication of signals between the processing system 106 and the imaging assembly 110 included in the IVUS device 102. This communication includes the steps of: (1) providing commands to integrated circuit controller chip(s) 206A, 206B, illustrated in FIG. 2, included in the imaging assembly 110 to select the particular transducer array element(s) to be used for transmit and receive, (2) providing the transmit trigger signals to the integrated circuit controller chip(s) 206A, 206B included in the imaging assembly 110 to activate the transmitter circuitry to generate an electrical pulse to excite the selected transducer array element(s), and/or (3) accepting amplified echo signals received from the selected transducer array element(s) via amplifiers included on the integrated circuit controller chip(s) of the imaging assembly 110. In some embodiments, the PIM 104 performs preliminary processing of the echo data prior to relaying the data to the processing system 106. In examples of such embodiments, the PIM 104 performs amplification, filtering, and/or aggregating of the data. In an embodiment, the PIM 104 also supplies high- and low-voltage DC power to support operation of the IVUS device 102 including circuitry within the imaging assembly 110.

The processing system 106 receives the echo data from the imaging assembly 110 by way of the PIM 104 and processes the data to reconstruct an image of the tissue structures in the medium surrounding the imaging assembly 110. The processing system 106 outputs image data such that an image of the vessel 120, such as a cross-sectional image of the vessel 120, is displayed on the monitor 108. Vessel 120 may represent fluid filled or surrounded structures, both natural and man-made. The vessel 120 may be within a body of a patient. The vessel 120 may be a blood vessel, as an artery or a vein of a patient's vascular system, including cardiac vasculature, peripheral vasculature, neural vasculature, renal vasculature, and/or or any other suitable lumen inside the body. For example, the IVUS device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the IVUS device 102 may be used to examine man-made structures such as, but without limitation, heart valves, stents, shunts, filters and other devices.

Figure 2:
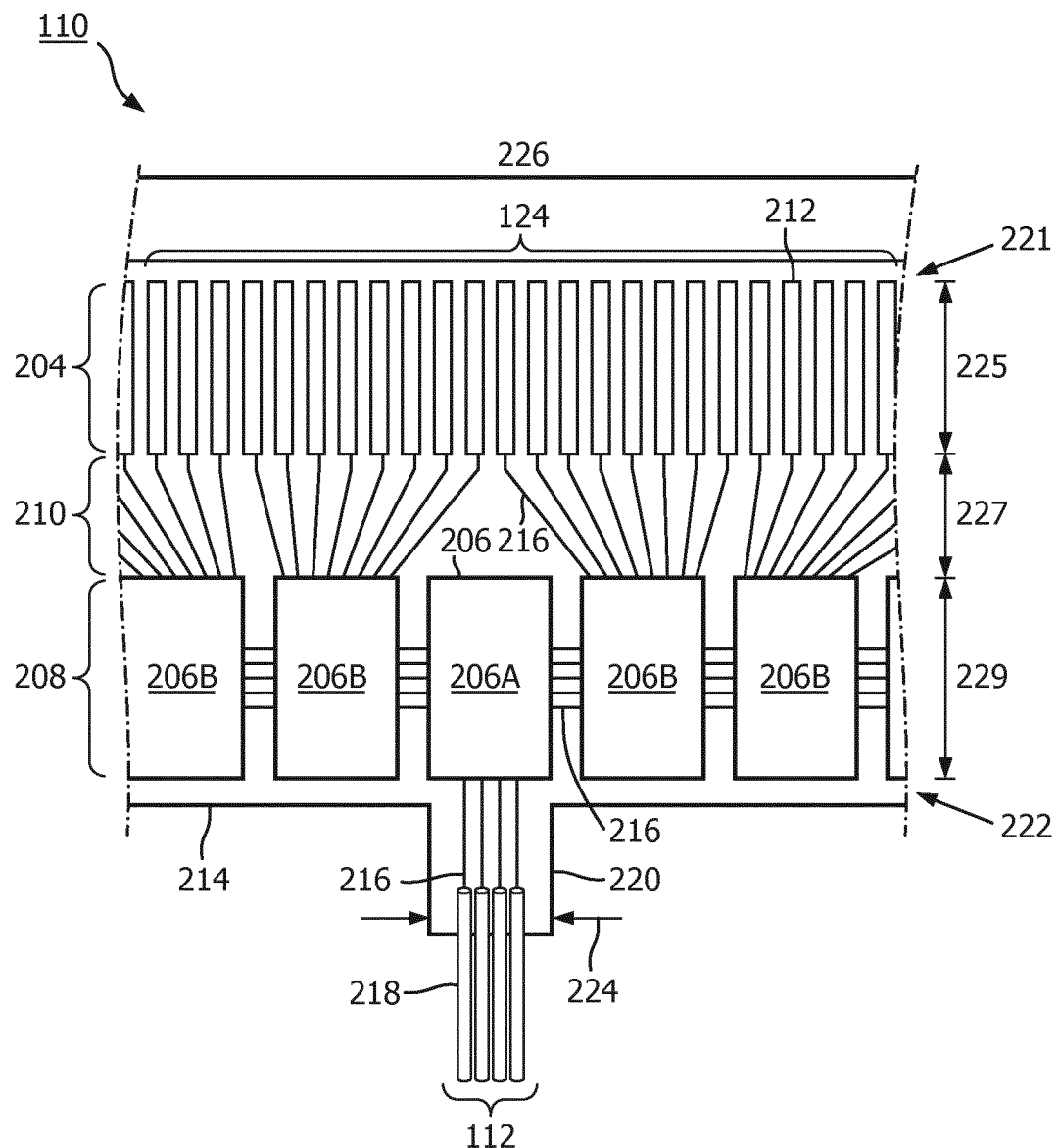
FIG. 2 is a diagrammatic top view of an imaging assembly in a flat configuration, according to aspects of the present disclosure.

In some embodiments, the IVUS device includes some features similar to traditional solid-state IVUS catheters, such as the EagleEye® catheter available from Volcano Corporation and those disclosed in U.S. Pat. No. 7,846,101 hereby incorporated by reference in its entirety. For example, the IVUS device 102 includes the imaging assembly 110 near a distal end of the IVUS device 102 and an electrical cable 112 extending along the longitudinal body of the IVUS device 102. The electrical cable 112 can include a plurality of conductors, including one, two, three, four, five, six, seven, or more conductors 218 (FIG. 2). It is understood that any suitable gauge wire can be used for the conductors 218. In an embodiment, the electrical cable 112 can include a four-conductor transmission line arrangement with, e.g., 41 AWG gauge wires. In an embodiment, the electrical cable 112 can include a seven-conductor transmission line arrangement utilizing, e.g., 44 AWG gauge wires. In some embodiments, 43 AWG gauge wires can be used.

The electrical cable 112 terminates in a PIM connector 114 at a proximal end of the IVUS device 102. The PIM connector 114 electrically couples the electrical cable 112 to the PIM 104 and physically couples the IVUS device 102 to the PIM 104. In an embodiment, the IVUS device 102 further includes a guide wire exit port 116. Accordingly, in some instances the IVUS device is a rapid-exchange catheter. The guide wire exit port 116 allows a guide wire 118 to be inserted towards the distal end in order to direct the device 102 through the vessel 120.

The IVUS device 102 includes a flexible elongate member 115 having a proximal portion and a distal portion. The imaging assembly 110 is positioned at a distal portion of the flexible elongate member 115. The flexible elongate member 115 includes a longitudinal axis LA. The longitudinal axis LA may be associated with the IVUS device 102 and/or the imaging assembly 110.

Figure 3:
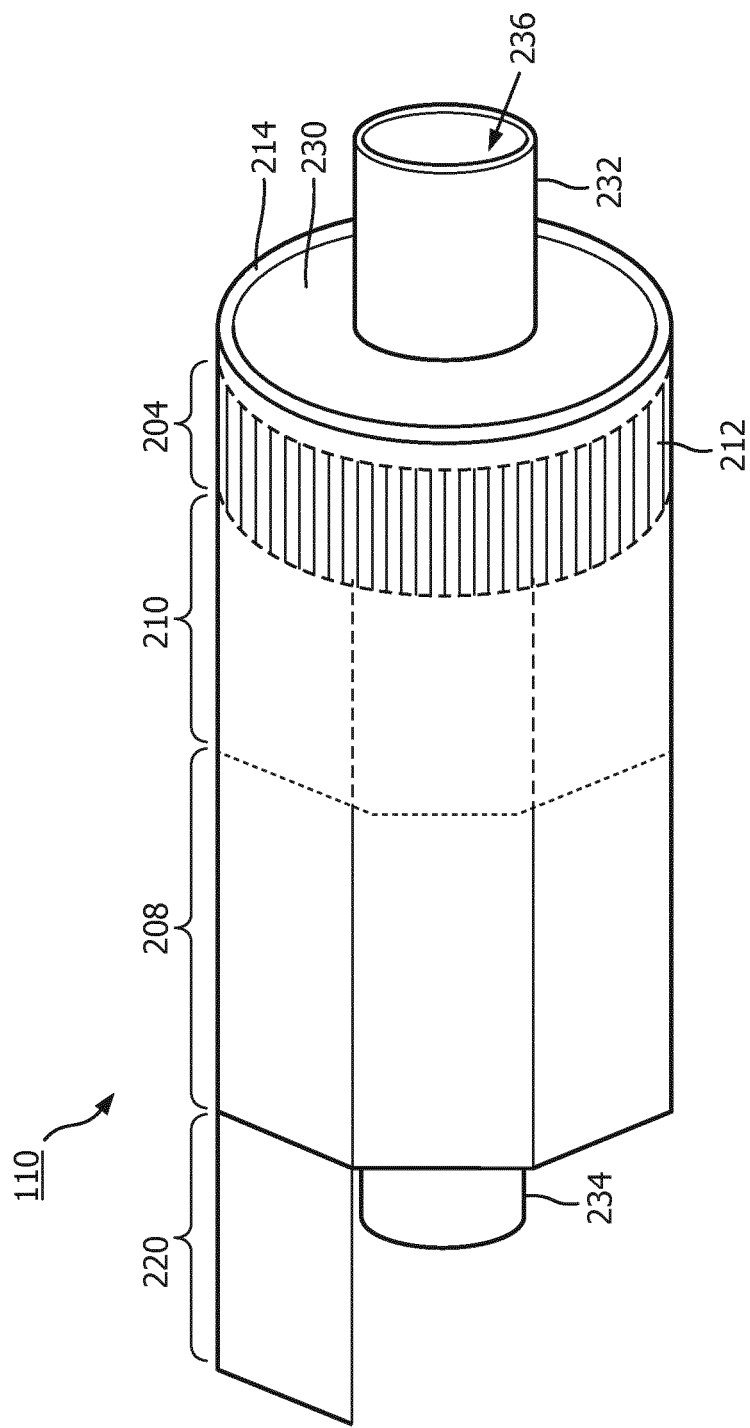
FIG. 3 is a diagrammatic side view of an imaging assembly in a rolled configuration around a tubular member, according to aspects of the present disclosure.

FIG. 2 is a top view of a portion of an ultrasound imaging assembly 110 according to an embodiment of the present disclosure. The imaging assembly 110 includes a transducer array 124 formed in a transducer region 204 and transducer control logic dies 206 (including dies 206A and 206B) formed in a control region 208, with a transition region 210 disposed therebetween. The transducer control logic dies 206 and the transducers 212 are mounted on a flexible substrate 214 that is shown in a flat configuration in FIG. 2. FIG. 3 illustrates a rolled configuration of the flexible substrate 214. The transducer array is a non-limiting example of a medical sensor element and/or a medical sensor element array. The transducer control logic dies 206 is a non-limiting example of a control circuit. The transducer region 204 is disposed adjacent a distal portion 221 of the flexible substrate 214. The control region 208 is disposed adjacent the proximal portion 222 of the flexible substrate 214. The transition region 210 is disposed between the control region 208 and the transducer region 204. Dimensions of the transducer region 204, the control region 208, and the transition region 210 (e.g., lengths 225, 227, 229) can vary in different embodiments. In some embodiments, the lengths 225, 227, 229 can be substantially similar or a length 227 of the transition region 210 can be greater than lengths 225, 229 of the transducer region and controller region, respectively. While the imaging assembly 110 is described as including a flexible substrate, it is understood that the transducers and/or controllers may be arranged to form the imaging assembly 110 in other configurations, including those omitting a flexible substrate.

The transducer array 124 may include any number and type of ultrasound transducers 212, although for clarity only a limited number of ultrasound transducers are illustrated in FIG. 2. In an embodiment, the transducer array 124 includes 64 individual ultrasound transducers 212. In a further embodiment, the transducer array 124 includes 32 ultrasound transducers 212. Other numbers are both contemplated and provided for. With respect to the types of transducers, in an embodiment, the ultrasound transducers 212 are piezoelectric micromachined ultrasound transducers (PMUTs) fabricated on a microelectromechanical system (MEMS) substrate using a polymer piezoelectric material, for example as disclosed in U.S. Pat. No. 6,641,540, which is hereby incorporated by reference in its entirety. In alternate embodiments, the transducer array includes piezoelectric zirconate transducers (PZT) transducers such as bulk PZT transducers, capacitive micromachined ultrasound transducers (cMUTs), single crystal piezoelectric materials, other suitable ultrasound transmitters and receivers, and/or combinations thereof.

The imaging assembly 110 may include various transducer control logic, which in the illustrated embodiment is divided into discrete control logic dies 206. In various examples, the control logic of the imaging assembly 110 performs: decoding control signals sent by the PIM 104 across the electrical cable 112, driving one or more transducers 212 to emit an ultrasonic signal, selecting one or more transducers 212 to receive a reflected echo of the ultrasonic signal, amplifying a signal representing the received echo, and/or transmitting the signal to the PIM across the electrical cable 112. In the illustrated embodiment, a imaging assembly 110 having 64 ultrasound transducers 212 divides the control logic across nine control logic dies 206, of which five are shown in FIG. 2. Designs incorporating other numbers of control logic dies 206 including 8, 9, 16, 17 and more are utilized in other embodiments. In general, the control logic dies 206 are characterized by the number of transducers they are capable of driving, and exemplary control logic dies 206 drive 4, 8, and/or 16 transducers.

The control logic dies are not necessarily homogenous. In some embodiments, a single controller is designated a master control logic die 206A and contains the communication interface for the electrical cable 112. Accordingly, the master control circuit may include control logic that decodes control signals received over the electrical cable 112, transmits control responses over the electrical cable 112, amplifies echo signals, and/or transmits the echo signals over the electrical cable 112. The remaining controllers are slave controllers 206B. The slave controllers 206B may include control logic that drives a transducer 212 to emit an ultrasonic signal and selects a transducer 212 to receive an echo. In the depicted embodiment, the master controller 206A does not directly control any transducers 212. In other embodiments, the master controller 206A drives the same number of transducers 212 as the slave controllers 206B or drives a reduced set of transducers 212 as compared to the slave controllers 206B. In an exemplary embodiment, a single master controller 206A and eight slave controllers 206B are provided with eight transducers assigned to each slave controller 206B.

The flexible substrate 214, on which the transducer control logic dies 206 and the transducers 212 are mounted, provides structural support and interconnects for electrical coupling. The flexible substrate 214 may be constructed to include a film layer of a flexible polyimide material such as KAPTON™ (trademark of DuPont). Other suitable materials include polyester films, polyimide films, polyethylene napthalate films, or polyetherimide films, other flexible printed semiconductor substrates as well as products such as Upilex® (registered trademark of Ube Industries) and TEFLON® (registered trademark of E.I. du Pont). In the flat configuration illustrated in FIG. 2, the flexible substrate 214 has a generally rectangular shape. As shown and described herein, the flexible substrate 214 is configured to be wrapped around a tubular member 230 (FIG. 3) to form a cylindrical toroid in some instances. Therefore, the thickness of the film layer of the flexible substrate 214 is generally related to the degree of curvature in the final assembled imaging assembly 110. In some embodiments, the film layer is between 5 μm and 100 μm, with some particular embodiments being between 12.7 μm and 25.1 μm.

To electrically interconnect the control logic dies 206 and the transducers 212, in an embodiment, the flexible substrate 214 further includes conductive traces 216 formed on the film layer that carry signals between the control logic dies 206 and the transducers 212. In particular, the conductive traces 216 providing communication between the control logic dies 206 and the transducers 212 extend along the flexible substrate 214 within the transition region 210. In some instances, the conductive traces 216 can also facilitate electrical communication between the master controller 206A and the slave controllers 206B. The conductive traces 216 can also provide a set of conductive pads that contact the conductors 218 of cable 112 when the conductors 218 of the electrical cable 112 are mechanically and electrically coupled to the flexible substrate 214. Suitable materials for the conductive traces 216 include copper, gold, aluminum, silver, tantalum, nickel, and tin, and may be deposited on the flexible substrate 214 by processes such as sputtering, plating, and etching. In an embodiment, the flexible substrate 214 includes a chromium adhesion layer. The width and thickness of the conductive traces 216 are selected to provide proper conductivity and resilience when the flexible substrate 214 is rolled. In that regard, an exemplary range for the thickness of a conductive trace 216 and/or conductive pad is between 10-50 µm. For example, in an embodiment, 20 µm conductive traces 216 are separated by 20 µm of space. The width of a conductive trace 216 on the flexible substrate 214 may be further determined by the width of the conductor 218 to be coupled to the trace/pad.

The flexible substrate 214 can include a connection interface 220 in some embodiments. The connection interface 220 can be a location of the flexible substrate 214 where the conductors 218 of the electrical cable 112 are coupled to the flexible substrate 214. For example, the bare conductors of the electrical cable 112 are electrically coupled to the flexible substrate 214 at the connection interface 220. The connection interface 220 can be a tab extending from the main body of flexible substrate 214. In that regard, the main body of the flexible substrate 214 can refer collectively to the transducer region 204, controller region 208, and the transition region 210. In the illustrated embodiment, the connection interface 220 extends from the proximal portion 222 of the flexible substrate 214. In other embodiments, the connection interface 220 is positioned at other parts of the flexible substrate 214, such as the distal portion 221, or the flexible substrate 214 omits the connection interface 220. A value of a dimension of the tab or connection interface 220, such as a width 224, can be less than the value of a dimension of the main body of the flexible substrate 214, such as a width 226. In some embodiments, the substrate forming the connection interface 220 is made of the same material(s) and/or is similarly flexible as the flexible substrate 214. In other embodiments, the connection interface 220 is made of different materials and/or is comparatively more rigid than the flexible substrate 214. For example, the connection interface 220 can be made of a plastic, thermoplastic, polymer, hard polymer, etc., including polyoxymethylene (e.g., DELRIN®), polyether ether ketone (PEEK), nylon, and/or other suitable materials. As described in greater detail herein, the tubular member 230, the flexible substrate 214, the connection interface 220 and/or the conductor(s) 218 can be variously configured to facilitate efficient manufacturing and operation of the imaging assembly 110.

Figure 4:
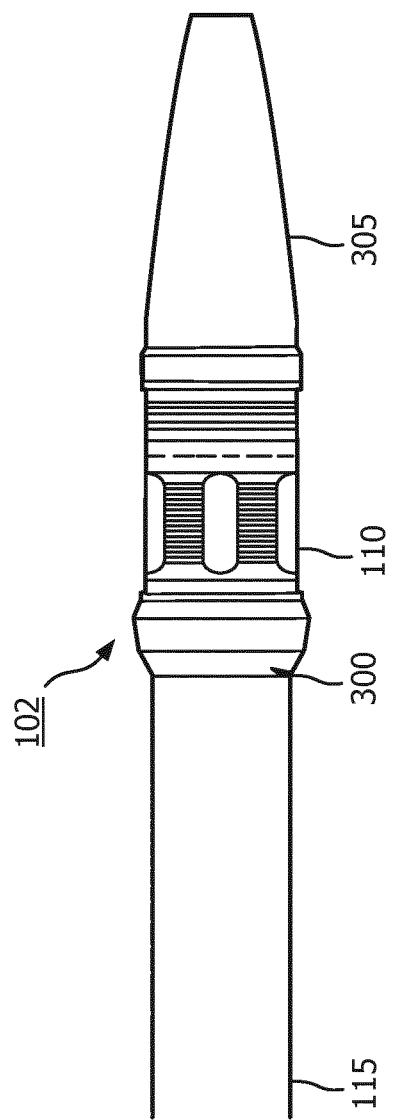
FIG. 4 is a diagrammatic side view of an IVUS device, according to aspects of the present disclosure.

In some instances, the imaging assembly 110 is transitioned from a flat configuration (FIG. 2) to a rolled or more cylindrical configuration (FIGS. 3 and 4). For example, in some embodiments, techniques are utilized as disclosed in one or more of U.S. Pat. No. 6,776,763, titled "ULTRASONIC TRANSDUCER ARRAY AND METHOD OF MANUFACTURING THE SAME" and U.S. Pat. No. 7,226,417, titled "HIGH RESOLUTION INTRAVASCULAR ULTRASOUND TRANSDUCER ASSEMBLY HAVING A FLEXIBLE SUBSTRATE," each of which is hereby incorporated by reference in its entirety.

As shown in FIG. 3, the flexible substrate 214 is positioned around the tubular member 230 in the rolled configuration. FIG. 3 is a diagrammatic side view with the flexible substrate 214 in the rolled configuration around the tubular member 230, according to aspects of the present disclosure. The tubular member 230 can be referenced as a unibody in some instances. The tubular member 230 can be composed of a metallic material, such as stainless steel, or non-metallic material, such as a plastic or polymer as described in U.S. Provisional Application No. 61/985,220, "Pre-Doped Solid Substrate for Intravascular Devices," filed Apr. 28, 2014, the entirety of which is hereby incorporated by reference herein. The tubular member 230 can have a distal section 232, a proximal section 234, and a lumen 236 extending longitudinally therethrough. The lumen 236 can be in communication with the exit port 116 and is sized and shaped to receive the guide wire 118 (FIG. 1). The tubular member 230 can be manufactured accordingly to any suitable process. For example, the tubular member 230 can be machined, such as by removing material from a blank to shape the tubular member 230, or molded, such as by an injection molding process. In some embodiments, the tubular member 230 may be integrally formed as a unitary structure, while in other embodiments the tubular member 230 may be formed of different components.

FIG. 4 illustrates an IVUS device 102 according to an exemplary embodiment of the present disclosure. The IVUS device 102 includes an imaging assembly 110, a tip 305, a support member 300, and a flexible elongate member 115. The flexible elongate member 115 can include a flexible outer catheter shaft and/or a flexible inner member. The imaging assembly 110 is connected to the flexible elongate member 115 through the support member 300. In some embodiment, as shown in FIG. 4, a distal portion of flexible elongate member 115 is pre-flared to receive the support member 300 therewithin, resulting in a relatively large diameter near or at the distal portion of flexible elongate member 115 compared to more proximal portions. However, in some other embodiments not shown in FIG. 4, an outer diameter of flexible elongate member and an outer diameter of imaging assembly 110 are of substantially the same diameter when support member 300 is received within the distal portion of flexible elongate member 115. In some embodiments, the support member 300 is made of a metal or metal alloy. In some other embodiments, the support member 300 is made of plastic or polymer, such as Pebax®, polyethylene (PE), polyethylene terephthalate (PET), polyimide (PI), polyester or a blend thereof. In some embodiments, the support member 300 is a concentric composite of two layers of materials to achieve flexibility. The support member 300 can be structured to allow more adhesion surface for adhesive to provide durability, flexibility, and a complete electrical seal at the junction while maintaining a low catheter profile.

Figure 5:
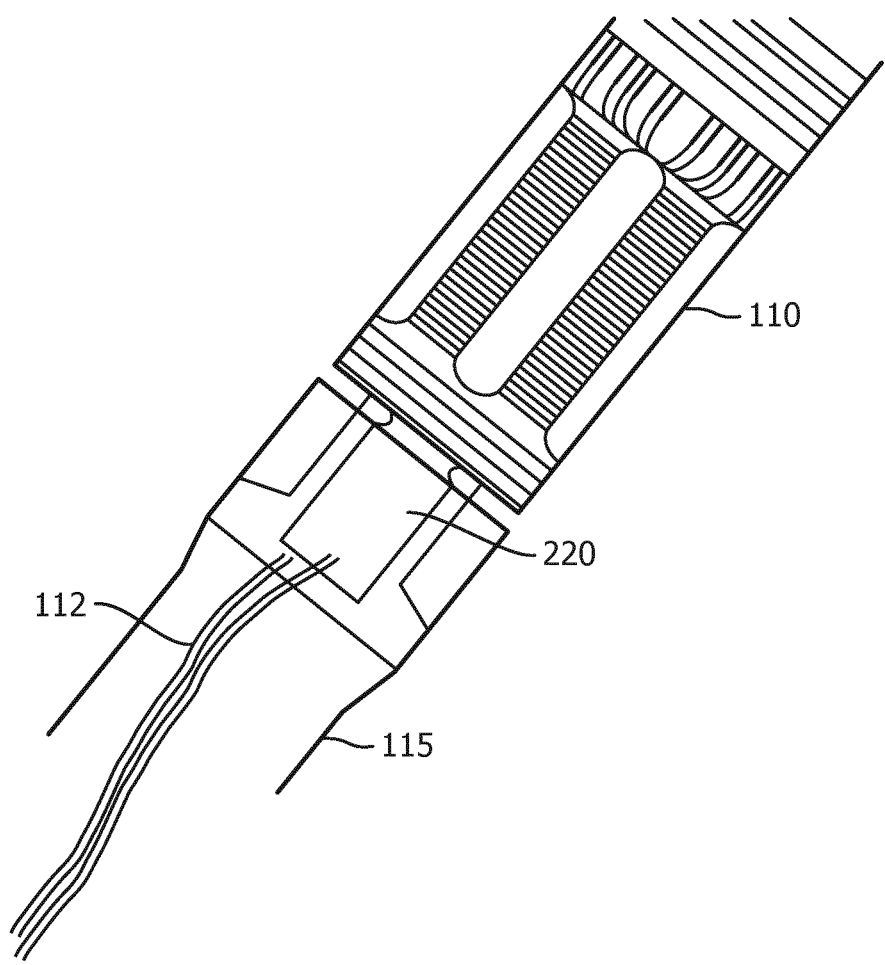
FIG. 5 is an image of a junction between a flexible elongate member and an imaging assembly, according to aspects of the present disclosure.

FIG. 5 is an image of the junction between to a flexible elongate member 115 and an imaging assembly 110. As can be seen through the translucent flexible elongate member 115, a connection interface 220 from the imaging assembly 110 is bonded to an electrical cable 112. The electrical cable 112 extends along a length of the flexible elongate member 115. Connection interface 220 and electrical cable 112 are also shown in FIG. 2.

Figure 6:
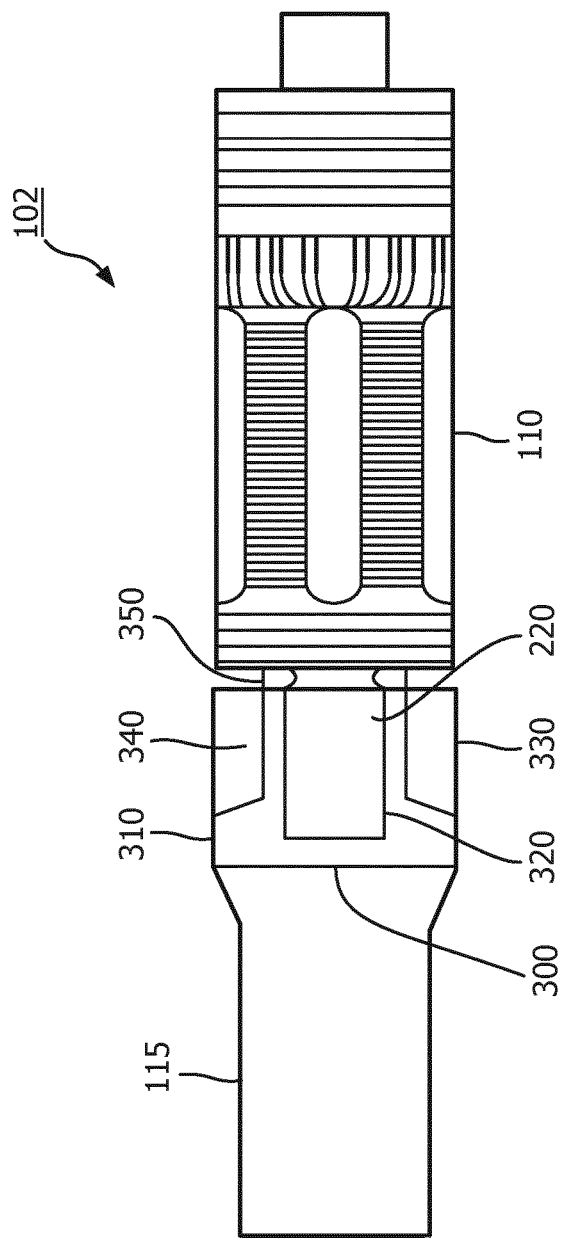
FIG. 6 is a diagrammatic side view of a junction between a flexible elongate member and an imaging assembly, according to aspects of the present disclosure.
Figure 7:
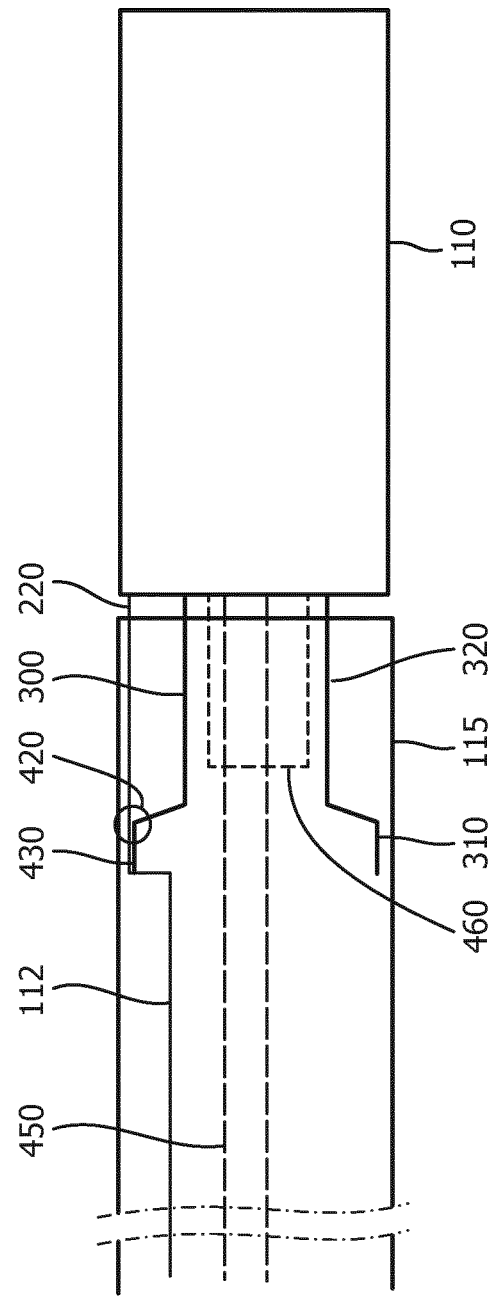
FIG. 7 is a diagrammatic side view of a junction between a flexible elongate member and an imaging assembly, according to aspects of the present disclosure.
Figure 8:
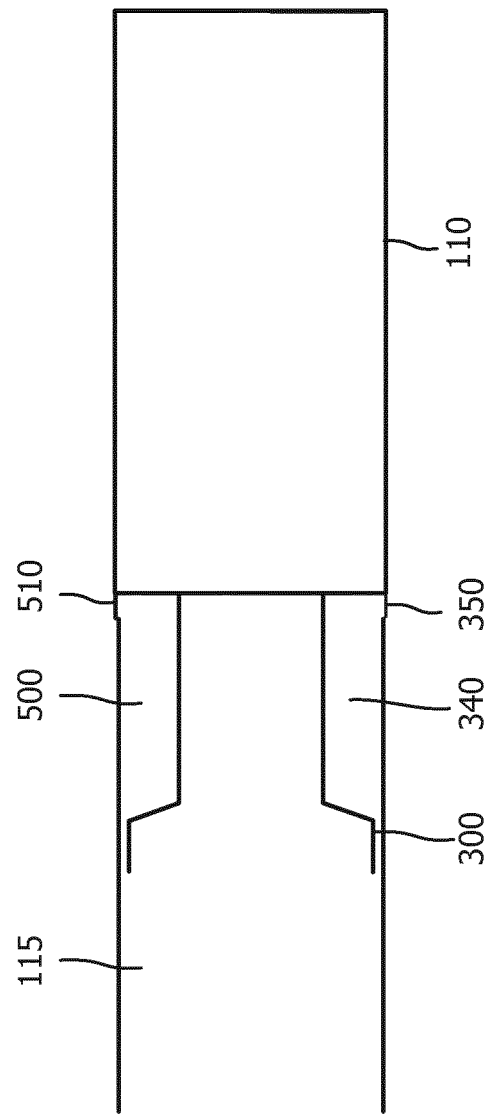
FIG. 8 is a diagrammatic side view of a junction between a flexible elongate member and an imaging assembly, according to aspects of the present disclosure.

Referring now to FIGS. 6, 7, and 8, shown therein are aspects of the junction between the imaging assembly 110 and the flexible elongate member 115 of an intraluminal imaging device according to the present disclosure. In particular, FIG. 6 is a diagrammatic side view of a junction between the flexible elongate member 115 and the imaging assembly 110; FIG. 7 is a diagrammatic side see-through view of the junction between the flexible elongate member 115 and the imaging assembly 110; and FIG. 8 is a diagrammatic side view of the junction between the flexible elongate member 115 and the imaging assembly 110. FIGS. 6, 7, and 8 illustrate various features of the support member 300 and how the support member 300 interfaces with different components of the IVUS device 102 according to aspects of the present disclosure.

As shown in FIG. 6, the support member 300 includes a proximal section 310 and a distal section 320. The distal section 320 has a diameter that is smaller than that of the proximal section 310. In some embodiments, both the proximal section 310 and distal section 320 are cylindrical with uniform diameters throughout their respective lengths. This design includes a stepped change of diameters when the proximal section 310 transitions into the distal section 320. In some embodiments, the distal section 320 is a conical taper and transitions from a diameter at the transition point near the proximal section 310 to a smaller diameter at a distal end of the distal section 320. In some other embodiments, the side profile of the distal section 320 has different features to enhance adhesive adhesion or mechanical strength of the junction between the flexible elongate member 115 and the imaging assembly 110. For example, the side profile of the distal section 320 can have ridges (not shown).

When assembled, the proximal section 310 engages or contacts at least a portion of the flexible elongate member 115 and the distal end of the distal section 320 engages or contacts a proximal end of the imaging assembly 110. The connection interface 220 extends from the imaging assembly 110 and over the support member 300. As shown in FIG. 6, in some embodiments, the connection interface 220 extends over the distal section 320 and a portion of the proximal section 310. In some embodiments, the connection interface 220 only extends over the distal section 320 or a portion of the distal section 320. In some embodiments, the connection interface 220 is mounted on the support member 300. For example, the connection interface 220 can be mounted on an outer surface of the proximal section 310.

The distal-facing surface of the proximal section 310, the outer surface of the distal section 320, and the inner surface of the distal portion 330 of the flexible elongate member 115 form an annular lumen 340. As can be seen from FIG. 6, the annular lumen 340 is ring-shaped or donut-shaped when the distal section 320 is cylindrical with a uniform diameter along its length. When the side profile of the distal section 320 is a conical taper or contains other features, the resulting annular lumen 340 would have a corresponding or reciprocal shape. When the distal end of the distal section 320 engages or is coupled to the proximal end of the imaging assembly 110, the distal end of the flexible elongate member 115 is separated from the proximal end of the imaging assembly 110 by a gap 350. The gap 350 is in fluid communication with the annular lumen 340 such that when adhesive is supplied through the gap 350, the adhesive fills the annular lumen 340 and eventually the gap 350 as well. In some embodiments, the gap is about 0.5 mm.

As shown in FIG. 7, in some embodiments, the support member 300 includes a lumen extending longitudinally through the proximal section 310 and the distal section 320. In some embodiments, the imaging assembly 110 includes a tubular member 460 extending proximally from the proximal end of the imaging assembly 110. The support member 300 is configured to receive the tubular member 460. To strengthen the coupling between the tubular member 460 and the support member 300, in some embodiments, the inner surface of the lumen is treated by plasma or with other surface roughening processes. In some embodiments, the surface roughening processes include application of a surface treatment agent, such as a primer. In some embodiments, the connection interface 220 extends towards the flexible elongate member 115 and is bonded to the electrical cable 112 at the connection point 420. In some embodiments, the electrical cable 112 is threaded through an opening 430 on or near the proximal section 310 of the support member 300. The opening 430 is adjacent to the connection point 420. In some embodiments, the electrical cable 112 extends over the proximal section 310 between the proximal section 310 and the inner surface of the flexible elongate member 115 and the support member 300 does not have the opening 430. In some embodiments, an inner member 450 extends through the flexible elongate member 115, the lumen within the support member 300, and the tubular member 460. The inner member 450 is configured to receive a guidewire such that the IVUS device 102 can travel along the guidewire to the target location in a patient's vessel.

FIG. 8 illustrates how the adhesive 500 fills the annular lumen 340 and the gap 350. The adhesive 500 is supplied through the gap 350 and fills both the annular lumen 340 and the gap 350. In some embodiments, the adhesive 500 in the annular lumen 340 and the gap 350 needs to be cured. In some embodiments, the adhesive 500 is water-curable and is cured by being exposed to moisture. In other embodiments, the adhesive 500 is thermal-curable and is cured by being exposed to a heat source at a temperature substantially higher than room temperature. In still other embodiments, the adhesive 500 is UV-curable and is cured by being exposed to ultraviolet (UV) light from a UV source. As shown in FIG. 5, the flexible elongate member 115 is translucent and when the imaging device is exposed to UV, UV energy can effectively go through the flexible elongate member 115 and cure the adhesive 500 within the annular lumen 340. The adhesive in the gap 350 has an outer surface 510. The outer surface 510 is substantially level and coplanar with the outer surface of the flexible elongate member 115 and the outer surface of the imaging assembly 110. The adhesive 500 is flexible when it is cured. For example, the adhesive 500 can be acrylic, epoxy-based, or cyanoacrylate.

Figure 9A:
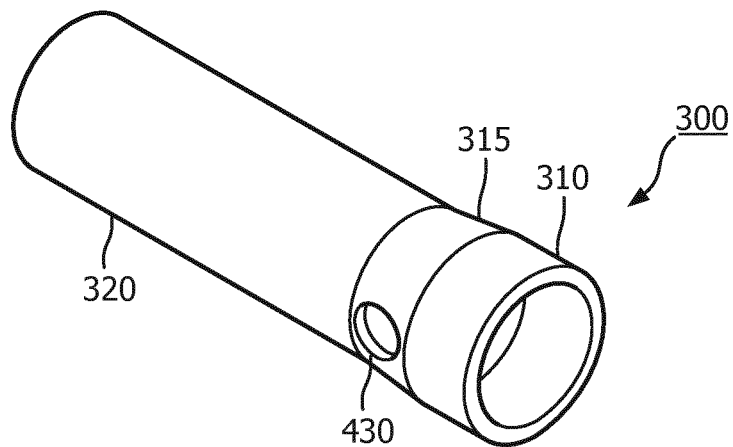
FIG. 9A is a diagrammatic perspective view of a support member, according to aspects of the present disclosure.
Figure 9B:
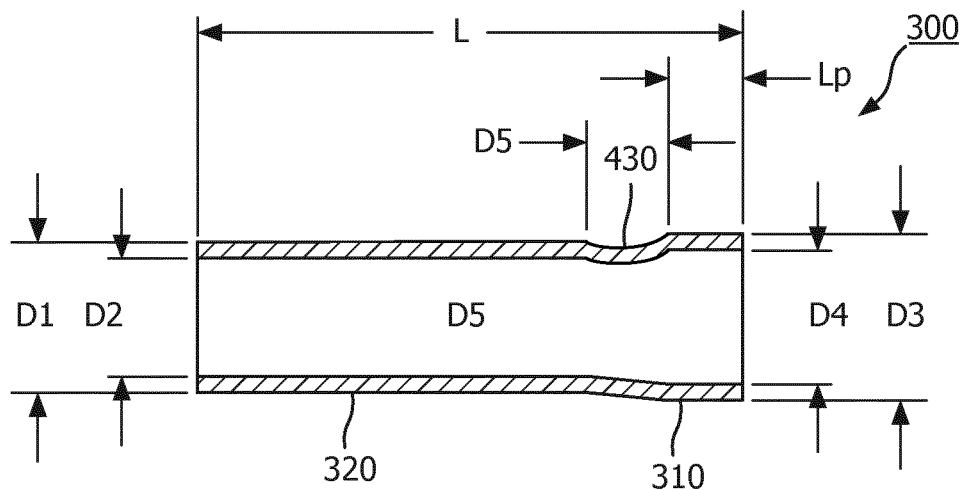
FIG. 9B is a diagrammatic side view of a support member, according to aspects of the present disclosure.
Figure 9C:
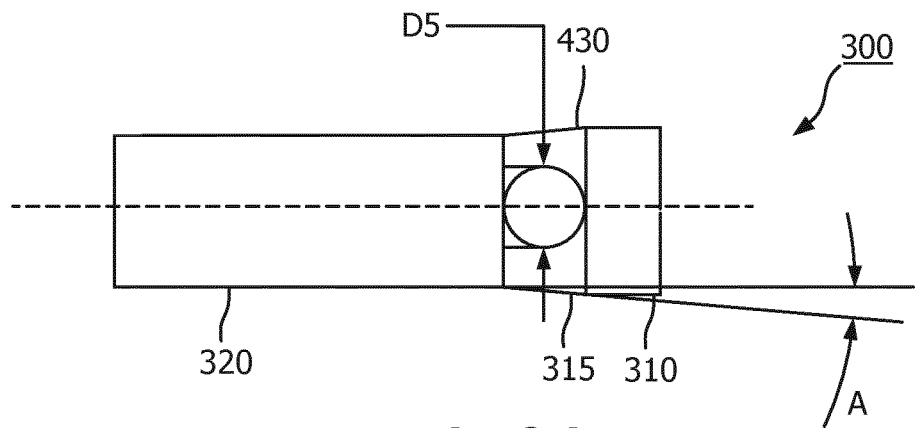
FIG. 9C is diagrammatic side view of a support member, according to aspects of the present disclosure.

Referring now FIGS. 9A, 9B, and 9C, shown therein are aspects of the support member 300 of an intraluminal imaging device. In particular, FIG. 9A is a diagrammatic perspective view of the support member 300; FIG. 9B is a diagrammatic side view of the support member 300; and FIG. 9C is diagrammatic side view of the support member 300. FIGS. 9A-9C illustrate various features of the support member 300 according to aspects of the present disclosure.

As shown in FIG. 9A, in some embodiments, the support member 300 includes the proximal section 310 that transitions to the distal section 320 via a taper section 315. In some embodiments, the support member 300 includes an opening 430. As described above in reference to FIG. 7, an electrical cable such as the electrical cable 112 can be threaded through the opening 430 to be bonded with the connection interface 220 (not shown in FIG. 9A). The opening 430 keeps secure the connection/bonding between the electrical cable 112 and the connection interface 220. As illustrated in FIG. 9A, because the opening of the opening 430 is tilted towards the distal section 320, any electrical cable threaded through the opening 430 undergoes minimum or no bending and is less prone to breakage or electrical shorts.

As illustrated in FIG. 9B, the support member 300 has a length L; the distal section 320 has an outer diameter D1 and an inner diameter D2; the proximal section 310 has a length Lp, an outer diameter D3 and an inner diameter D4; and the opening 430 has an diameter D5. In some embodiments, L is between approximately 0.060 and 0.157 inches. In some embodiments, Lp is between approximately 0.05 and 0.1 inches. In some embodiments, D1 is between approximately 0.030 and 0.035 inches and D2 is between approximately 0.025 and 0.030 inches. In some embodiments, D3 is between approximately 0.035 and 0.040 inches and D4 is between 0.030 and 0.035 inches. In some embodiments, D5 is between approximately 0.01 inches and approximately 0.02 inches, including values such as approximately 0.015 inches. In an exemplary embodiment, D1 is about 0.033 inches, D2 is about 0.027 inches, D3 is about 0.037 to 0.038 inches, and D is about 0.032 inches.

FIG. 9C is a diagrammatic side view of the support member 300. In some embodiments, the taper section 315 has a conical surface that extends from the proximal section 310 to the distal section 320. The conical surface has an inclined angle A. In some embodiments, A is between approximately 4 degrees and approximately 5.6 degrees, including values such as 4.8 degrees. In some embodiments, due to this inclined angle A, the opening of the opening 430 is tilted towards the distal section 320.

Figure 10:
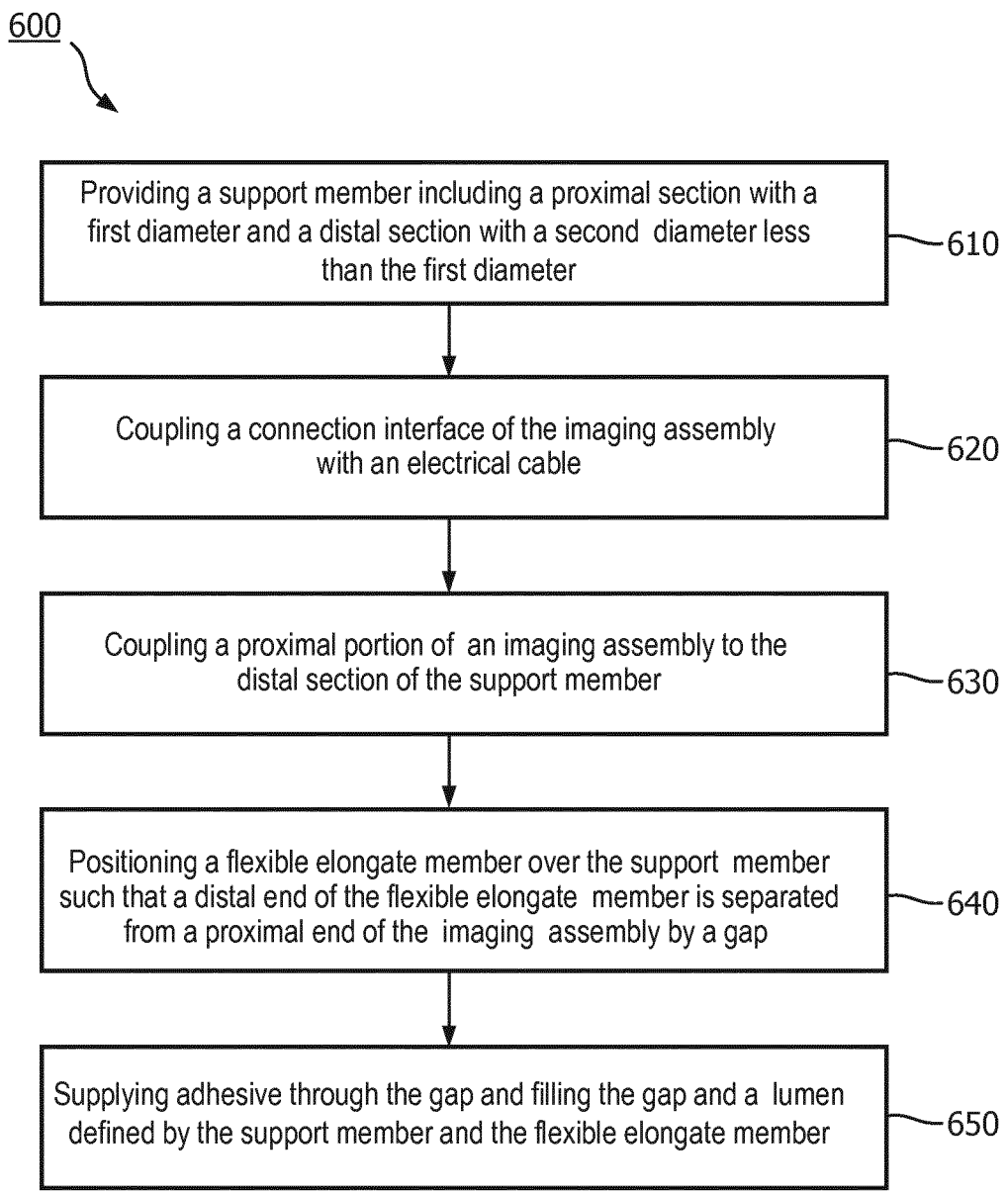
FIG. 10 is a flow diagram of a method of forming an intraluminal imaging device according to aspects of the present disclosure.

FIG. 10 shows a flow diagram of a method 600 of forming an intraluminal imaging device according to aspects of the present disclosure. The method 600 includes steps 610, 620, 630, 640, and 650. At step 610, a support member 300 is provided. The support member 300 includes a proximal section 310 with a first diameter and a distal section 320 with a second diameter less than the first diameter. At step 620, a connection interface 220 of the imaging assembly 110 is coupled to an electrical cable 112. In some embodiments, the electrical cable 112 goes through an opening 430 before being coupled to the connection interface 220. In those embodiments, step 620 includes threading the electrical cable 112 through the opening 430. At step 630, a proximal portion of an imaging assembly 110 is coupled to a distal section 320 of the support member 300. At step 640, the flexible elongate member 115 is positioned over the support member 300 such that a distal end of the flexible elongate member 115 is separated from a proximal end of the imaging assembly 110 by a gap 350. Finally, at step 650, an adhesive is supplied through the gap 350 and is allowed to fill the gap 350 and the annular lumen 340 defined by the support member 300 and the flexible elongate member 115. In some embodiments, the adhesive needs to be cured and step 650 includes curing the adhesive by heat, moisture or UV.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraluminal imaging device, comprising:
    a flexible elongate member configured for positioning within a body lumen of a patient;
    a support member coupled to the flexible elongate member; and
    a non-rotating imaging assembly coupled to the support member,
    wherein the support member includes a proximal section at a first end thereof configured to interface with a distal portion of the flexible elongate member and a distal section at a second end thereof configured to interface with a proximal end of the non-rotating imaging assembly, the proximal section comprising a first diameter, the distal section comprising a second diameter less than the first diameter,
    wherein the flexible elongate member is positioned over the support member;
    wherein the proximal section of the support member, the distal section of the support member, and the distal portion of the flexible elongate member define an annular lumen; and
    wherein the annular lumen is filled with an adhesive.

2. The intraluminal imaging device of claim 1, wherein a distal end of the flexible elongate member is spaced from the proximal end of the imaging assembly by a gap, the gap being in fluid communication with the annular lumen.

3. The intraluminal imaging device of claim 2, further comprising the adhesive disposed within the annular lumen and the gap.

4. The intraluminal imaging device of claim 1, wherein the support member comprises a lumen extending longitudinally through the proximal section and the distal section.

5. The intraluminal imaging device of claim 4, wherein the imaging assembly comprises a tubular member and a flexible substrate positioned around the tubular member, and wherein the lumen of the support member is configured to receive the tubular member.

6. The intraluminal imaging device of claim 5, wherein the lumen of the support member is further configured to receive an inner member configured to receive a guidewire.

7. The intraluminal imaging device of claim 4, wherein the support member further includes an opening extending through a wall in communication with the lumen, the opening configured to receive an electrical cable associated with the imaging assembly.

8. The intraluminal imaging device of claim 7, wherein a connection interface of the imaging assembly is mounted to an outer surface of the support member.

9. The intraluminal imaging device of claim 1, wherein the support member comprises a transition between the first diameter and the second diameter, the transition comprising a tapered region.

10. The intraluminal imaging device of claim 1, wherein the imaging assembly comprises an ultrasound transducer array.

11. The intraluminal imaging device of claim 1, further comprising:
    a connection interface configured to connect the flexible elongate member and the imaging assembly, the connection interface being disposed with the support member.

12. The intraluminal imaging device of claim 11, wherein the connection interface extends from the distal portion of the flexible elongate member.

13. The intraluminal imaging device of claim 12, wherein the connection interface comprises a tab.

14. The intraluminal imaging device of claim 11, further comprising an electrical cable configured to couple the connection interface to the imaging assembly.

15. The intraluminal imaging device of claim 14, wherein the electrical cable is electrically bonded to the connection interface.

16. An intraluminal imaging device, comprising: a solid-state intravascular ultrasound (IVUS) device including:
    a flexible elongate member configured for positioning within a body lumen of a patient;
    a support member coupled to the flexible elongate member;

a circumferential imaging assembly coupled to the support member and including an array of ultrasound transducer array elements distributed around a circumference of the circumferential imaging assembly; and at least one controller configured to excite selected one or more of the ultrasound transducer array elements to emit ultrasound energy and/or receive ultrasound echo signals from the selected one or more of the ultrasound transducer array elements;

wherein the support member includes a proximal section at a first end thereof connected with a distal portion of the flexible elongate member and a distal section at a second end thereof configured to interface with a proximal end of the circumferential imaging assembly, the proximal section comprising a first diameter, the distal section comprising a second diameter less than the first diameter;

wherein the flexible elongate member is positioned over the support member;

wherein the proximal section of the support member, the distal section of the support member, and the distal portion of the flexible elongate member define an annular lumen; and wherein the annular lumen is filled with an adhesive.

17. An intraluminal imaging device, comprising:

a flexible elongate member configured for positioning within a body lumen of a patient;

a support member coupled to the flexible elongate member; and an imaging assembly coupled to the support member, wherein the support member includes a proximal section configured to interface with a distal portion of the flexible elongate member and a distal section configured to interface with a proximal end of the imaging assembly, the proximal section comprising a first diameter, the distal section comprising a second diameter less than the first diameter;

wherein the flexible elongate member is positioned over the support member;

wherein the proximal section of the support member, the distal section of the support member, and the distal portion of the flexible elongate member define an annular lumen; and wherein the annular lumen is filled with an adhesive.

* * * * *